United States Patent [19]
Moss et al.

[11] Patent Number: 5,716,816
[45] Date of Patent: Feb. 10, 1998

[54] CLONES ENCODING MAMMALIAN ADP-RIBOSYLARGININE HYDROLASES

[75] Inventors: Joel Moss, Bethesda; Sally J. Stanley, Silver Spring; Maria S. Nightingale, Bethesda, all of Md.; Lucia Monaco, Rome, Italy; James J. Murtagh, Jr., Atlanta, Ga.; Tatsuyuki Takada, Rockville, Md.

[73] Assignee: The United States of America as represented by the Department of Health and Human Services, Washington, D.C.

[21] Appl. No.: 183,214

[22] Filed: Jan. 14, 1994

Related U.S. Application Data

[62] Division of Ser. No. 888,231, May 22, 1992, abandoned.

[51] Int. Cl.$^6$ .................... C12N 15/55; C12N 15/10; C12N 15/63; C12N 9/24
[52] U.S. Cl. .................. 435/172.3; 435/200; 435/69.1; 435/71.2; 435/240.2; 435/252.3; 435/252.33; 435/320.1; 536/23.1; 536/23.2; 935/14; 935/19; 935/29; 935/56; 935/79
[58] Field of Search ..................... 435/200, 69.1, 435/71.2, 172.3, 240.2, 252.3, 252.33, 320.1; 536/23.1, 23.2; 935/14, 19, 29, 56, 79

[56] References Cited

U.S. PATENT DOCUMENTS

| | | |
|---|---|---|
| 4,882,146 | 11/1989 | Shiells et al. |
| 5,108,919 | 4/1992 | Liu et al. .................. 435/224 |

OTHER PUBLICATIONS

Williamson, K.C., et al., "Mono-ADP-Riossyltransferases and ADP-Ribsoylarginine Hydrolasses: a Mono-ADP Ribosylation Cycle in Animal Cells," American Society for Microbiology, Washington, D.C., 25: 493-510 (1990).

Moss, J., et al., "Purification and Characterization of ADP-ribosylarginine Hydrolase from Turkey Erythrocytes," *Biochemistry*, 27: 5819-5823 (Jul. 26, 1988).

Moss J., et al., "Amino Acid specific ADP-ribosylation: Substrate Specificity of an ADP-ribosylarginine Hydrolase from Turkey Erythrocyres," *Biochemistry*, 25: 5408-5414 (Sep. 23, 1986).

Moss, J., et al., "Reversibility of arginine-specific mono (ADP-ribosyl)ation: Identification in erythrocytes of an ADP-ribose-L-arginine cleavage enzyme," *Proc. Natl. Acad. Sci. (USA)*, 82: 5603-5607 (Sep. 1985).

Moss, J., et al., "Purification and Characterization of Rat Brain ADP-Ribosylarginine Hydrolase," *FASEB J.*, 5(6): A1506, No. 6586, (Mar. 19, 1991).

Smith, K.P., et al., "Identification of Enzymatic Activities which Process Protein Bound Mono(ADP-Ribose)," *Biochemical and Biophysical Research Communications*, 126(1): 136-142 (Jan. 16, 1985).

Williamson, et al., "Mono-ADP-Ribosyltransferases and ADP-Ribosylarginine Hydrolases: a Mono-ADP Ribosylation Cycle in Animal Cells," *ADP-Ribosylating Toxins and G-Proteins*, Moss et al. (ed), Chap. 25, pp. 493-510, Amer. Soc. Microbiol. (1990).

Jacobson, et al., "Mono(ADP-Ribosylation) of Proteins at Arginine in vivo," *ADP-Ribosylation of Proteins*, Althaus et al. (ed), pp. 526-529, Springer-Verlag, Berlin (1985).

Moss, et al., "Isolation of an avian erythrocyte protein possessing ADP-ribosyltransferase activity and capable of activating adenylate cyclase," *Proc. Natl. Acad. Sci.*, 75(8): 3621-3624 (Aug. 1978).

Moss, et al., "Molecular and Immunological Characterization of ADP-ribosylarginine Hydrolases,"*J. Biol. Chem.*, 267(15): 10481-10488 (May 25, 1992).

Kim, et al., "Development of a High-Performance Liquid Chromatography Assay Method and Characterization of Adenosine Diphosphate-ribosylarginine Hydrolase in Skeletal Muscle," *Anal. Biochem.*, 187: 251-257 (1990).

Chang, et al., "Identification of an Enzymatic Activity that Hydrolyzes Protein-Bound ADP-Ribose in Skeletal Muscle," *Biochem. Biophys. Res. Comm.*, 139(3): 932-939 (Sep. 30, 1986).

Moss, J., et al., "Molecular and Immunological Characterization of ADP-Ribosylarginine Hydrolases," Abstract 10C from the Paul Mandel International Meeting on Poly (ADP-ribosyl)ation Reactions held from May 30, 1991-Jun. 3, 1991 in Quebec, Canada.

J. Moss et al., "Molecular and Immunological Characterization of ADP-ribosylarginine Hydrolases", ADP-Ribosylation Reactions, Guy G. Poirer et al. (editors) Springer-Verlag, New York, NY, pp. 389-392 (May 14, 1992).

M.P. Deutscher (ed.) "Guide to Protein Purification"Meth. Enzymol 182: 602-613, 738-751 (1990).

A. Belyavsky et al. "PCR-based cDNA Library Construction"Nuc. Acids. Res. 17(8) 2919-2932 (Apr. 1989).

S.L. Berger et al. (eds.) "Guide to Molecular Cloning Techniques"Meth. Enzymol. 152: 393-399, 415-423, 432-447, 663-704 (1987).

*Primary Examiner*—Rebecca E. Prouty
*Attorney, Agent, or Firm*—Townsend and Townsend and Crew

[57] ABSTRACT

The present invention relates to the production of mammalian ADP-ribosylarginine hydrolases. These enzymes can be manufactured using recombinant DNA technology and are useful in regulation of proteins involved in key metabolic pathways.

14 Claims, No Drawings

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 1245 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_signal
        ( B ) LOCATION: 1..26

( i x ) FEATURE:
        ( A ) NAME/KEY: CDS
        ( B ) LOCATION: 27..1115

( x i ) SEQUENCE DESCRIPTION: SEQ ID NO:1:

```
ATAAGACCGC CTGTGCCAAG CTCAGC ATG GGT GGG GGC CTG ATT GAG AGG TAT         53
                             Met Gly Gly Gly Leu Ile Glu Arg Tyr
                              1               5

GTG GCT GCC ATG GTG CTG AGT GCG GCT GGT GAT ACC CTG GGC TAC TTC        101
Val Ala Ala Met Val Leu Ser Ala Ala Gly Asp Thr Leu Gly Tyr Phe
```

|  |  |  |  |  |  |  |  |  |  |  |  |  |  |  |  |
|---|---|---|---|---|---|---|---|---|---|---|---|---|---|---|---|
| 10 |  |  |  |  | 15 |  |  |  |  | 20 |  |  |  |  | 25 |

```
AAC  GGG  AAG  TGG  GAA  TTC  CTT  CGG  GAT  GGG  GAG  AAG  ATA  CAC  CGG  CAG       149
Asn  Gly  Lys  Trp  Glu  Phe  Leu  Arg  Asp  Gly  Glu  Lys  Ile  His  Arg  Gln
                         30                        35                    40

TTG  GCC  CAG  ATG  GGT  GAC  TTG  GAA  GCC  ATA  GAT  GTG  GCC  CAG  TGG  AGA       197
Leu  Ala  Gln  Met  Gly  Asp  Leu  Glu  Ala  Ile  Asp  Val  Ala  Gln  Trp  Arg
                    45                        50                    55

GTC  AGC  GAT  GAC  ACC  ATC  ATG  CAC  CTG  GCT  ACA  GCA  GAA  GCC  CTC  ATG       245
Val  Ser  Asp  Asp  Thr  Ile  Met  His  Leu  Ala  Thr  Ala  Glu  Ala  Leu  Met
               60                   65                        70

GAA  GCC  GGC  AGT  TCC  CCG  GAT  TTG  CCT  CAG  CTG  TAT  TCC  CTA  CTA  GCT       293
Glu  Ala  Gly  Ser  Ser  Pro  Asp  Leu  Pro  Gln  Leu  Tyr  Ser  Leu  Leu  Ala
     75                        80                   85

AAA  CAT  TAC  CGG  GAC  TGC  ATG  GGA  GAC  ATG  GAT  GGC  CGG  GCA  CCA  GGT       341
Lys  His  Tyr  Arg  Asp  Cys  Met  Gly  Asp  Met  Asp  Gly  Arg  Ala  Pro  Gly
90                        95                        100                       105

GGT  GCT  TGC  ATG  CAG  AAT  GCC  ATG  CAG  CTG  GAC  CCC  GAC  AGG  GCT  GAC       389
Gly  Ala  Cys  Met  Gln  Asn  Ala  Met  Gln  Leu  Asp  Pro  Asp  Arg  Ala  Asp
                              110                       115                  120

GGC  TGG  AGG  ATT  CCC  TTC  AAC  AGT  CAC  GAG  GGC  GGC  TGT  GGA  GCC  GCC       437
Gly  Trp  Arg  Ile  Pro  Phe  Asn  Ser  His  Glu  Gly  Gly  Cys  Gly  Ala  Ala
                    125                       130                       135

ATG  CGC  GCC  ATG  TGC  ATC  GGG  CTG  AGG  TTT  CCT  CAC  CCC  AGC  CAG  CTG       485
Met  Arg  Ala  Met  Cys  Ile  Gly  Leu  Arg  Phe  Pro  His  Pro  Ser  Gln  Leu
          140                       145                       150

GAC  ACT  CTG  ATC  CAA  GTG  AGC  ATC  GAG  AGC  GGC  CGG  ATG  ACC  CAC  CAC       533
Asp  Thr  Leu  Ile  Gln  Val  Ser  Ile  Glu  Ser  Gly  Arg  Met  Thr  His  His
               155                       160                       165

CAC  CCC  ACA  GGC  TAC  CTC  GGA  AGC  CTA  GCG  TCA  GCT  CTT  TTT  ACC  GCA       581
His  Pro  Thr  Gly  Tyr  Leu  Gly  Ser  Leu  Ala  Ser  Ala  Leu  Phe  Thr  Ala
170                       175                       180                       185

TAT  GCC  GTG  AAC  GGC  AAA  TCA  CCA  CGG  CAG  TGG  GGG  AAG  GGG  CTG  ATG       629
Tyr  Ala  Val  Asn  Gly  Lys  Ser  Pro  Arg  Gln  Trp  Gly  Lys  Gly  Leu  Met
                    190                       195                       200

GAG  GTG  CTG  CCA  GAG  GCC  AAA  GCG  TAT  GTC  ACC  CAG  TCA  GGC  TAC  TTT       677
Glu  Val  Leu  Pro  Glu  Ala  Lys  Ala  Tyr  Val  Thr  Gln  Ser  Gly  Tyr  Phe
               205                       210                       215

GTG  AAG  GAA  AAT  CTC  CAA  CAC  TGG  TCC  TAC  TTC  GAG  AAA  GAA  TGG  GAA       725
Val  Lys  Glu  Asn  Leu  Gln  His  Trp  Ser  Tyr  Phe  Glu  Lys  Glu  Trp  Glu
          220                       225                       230

AAG  TAC  CTG  GAA  CTT  AGA  GGA  ATT  TTG  GAT  GGC  AAG  TCC  GCT  CCC  GTC       773
Lys  Tyr  Leu  Glu  Leu  Arg  Gly  Ile  Leu  Asp  Gly  Lys  Ser  Ala  Pro  Val
     235                       240                       245

TTC  CCG  CAA  CCC  TTT  GGT  GTG  AAG  GAA  AGG  GAT  CAG  TTC  TAT  ATC  GAA       821
Phe  Pro  Gln  Pro  Phe  Gly  Val  Lys  Glu  Arg  Asp  Gln  Phe  Tyr  Ile  Glu
250                       255                       260                       265

GTG  AGC  TAC  TCA  GGC  TGG  GGT  GGC  AGC  AGT  GGA  CAC  GAT  GCC  CCC  ATG       869
Val  Ser  Tyr  Ser  Gly  Trp  Gly  Gly  Ser  Ser  Gly  His  Asp  Ala  Pro  Met
                    270                       275                       280

ATT  GCC  TAT  GAT  GCC  CTC  CTG  GCT  GCA  GGG  GAT  TCC  TGG  AAG  GAG  CTC       917
Ile  Ala  Tyr  Asp  Ala  Leu  Leu  Ala  Ala  Gly  Asp  Ser  Trp  Lys  Glu  Leu
               285                       290                       295

GCA  CAC  AGA  GCC  TTT  TTC  CAT  GGT  GGA  GAC  AGT  GAT  TCC  ACG  GCC  ACC       965
Ala  His  Arg  Ala  Phe  Phe  His  Gly  Gly  Asp  Ser  Asp  Ser  Thr  Ala  Thr
          300                       305                       310

ATT  GCT  GGA  TGC  TGG  TGG  GGA  GTT  ATG  CAC  GGT  TTC  AAA  GGG  GTA  AAC       1013
Ile  Ala  Gly  Cys  Trp  Trp  Gly  Val  Met  His  Gly  Phe  Lys  Gly  Val  Asn
     315                       320                       325

CCT  TCT  AAC  TAT  GAG  AAG  CTC  GAA  TAC  CGA  CAG  CGG  CTA  GAA  GAG  GCC       1061
Pro  Ser  Asn  Tyr  Glu  Lys  Leu  Glu  Tyr  Arg  Gln  Arg  Leu  Glu  Glu  Ala
```

```
                    330                 335                 340                 345
GGA AGA GCT TTG TAT TCT CTG GGG TCA AAA GAA GAC ACT ATA CTA GGT                        1109
Gly Arg Ala Leu Tyr Ser Leu Gly Ser Lys Glu Asp Thr Ile Leu Gly
                350                 355                 360

CCC TAGGGAAAGG GTGGTTTGTT TTGGCGGTTT TTTCCCTGT ATCCCCGACA                              1162
Pro

CTCATTCTCT TCAGCTTTTC CAGCGTCAAG AATCCTAATT TTGTGTTTGA AGAATTCTGT                      1222

GTAAACAAGT CCCTTGGGCG GCT                                                              1245
```

( 2 ) INFORMATION FOR SEQ ID NO:2:

( i ) SEQUENCE CHARACTERISTICS:
        ( A ) LENGTH: 362 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Gly Gly Gly Leu Ile Glu Arg Tyr Val Ala Ala Met Val Leu Ser
 1               5                  10                  15

Ala Ala Gly Asp Thr Leu Gly Tyr Phe Asn Gly Lys Trp Glu Phe Leu
            20                  25                  30

Arg Asp Gly Glu Lys Ile His Arg Gln Leu Ala Gln Met Gly Asp Leu
            35                  40                  45

Glu Ala Ile Asp Val Ala Gln Trp Arg Val Ser Asp Thr Ile Met
    50                  55                  60

His Leu Ala Thr Ala Glu Ala Leu Met Glu Ala Gly Ser Ser Pro Asp
 65                 70                  75                  80

Leu Pro Gln Leu Tyr Ser Leu Leu Ala Lys His Tyr Arg Asp Cys Met
                85                  90                  95

Gly Asp Met Asp Gly Arg Ala Pro Gly Gly Ala Cys Met Gln Asn Ala
            100                 105                 110

Met Gln Leu Asp Pro Asp Arg Ala Asp Gly Trp Arg Ile Pro Phe Asn
        115                 120                 125

Ser His Glu Gly Gly Cys Gly Ala Ala Met Arg Ala Met Cys Ile Gly
    130                 135                 140

Leu Arg Phe Pro His Pro Ser Gln Leu Asp Thr Leu Ile Gln Val Ser
145                 150                 155                 160

Ile Glu Ser Gly Arg Met Thr His His His Pro Thr Gly Tyr Leu Gly
                165                 170                 175

Ser Leu Ala Ser Ala Leu Phe Thr Ala Tyr Ala Val Asn Gly Lys Ser
            180                 185                 190

Pro Arg Gln Trp Gly Lys Gly Leu Met Glu Val Leu Pro Glu Ala Lys
        195                 200                 205

Ala Tyr Val Thr Gln Ser Gly Tyr Phe Val Lys Glu Asn Leu Gln His
    210                 215                 220

Trp Ser Tyr Phe Glu Lys Glu Trp Glu Lys Tyr Leu Glu Leu Arg Gly
225                 230                 235                 240

Ile Leu Asp Gly Lys Ser Ala Pro Val Phe Pro Gln Pro Phe Gly Val
                245                 250                 255

Lys Glu Arg Asp Gln Phe Tyr Ile Glu Val Ser Tyr Ser Gly Trp Gly
            260                 265                 270

Gly Ser Ser Gly His Asp Ala Pro Met Ile Ala Tyr Asp Ala Leu Leu
        275                 280                 285

Ala Ala Gly Asp Ser Trp Lys Glu Leu Ala His Arg Ala Phe Phe His
```

```
              290                          295                          300
Gly  Gly  Asp  Ser  Asp  Ser  Thr  Ala  Thr  Ile  Ala  Gly  Cys  Trp  Trp  Gly
305                      310                      315                      320

Val  Met  His  Gly  Phe  Lys  Gly  Val  Asn  Pro  Ser  Asn  Tyr  Glu  Lys  Leu
                    325                      330                      335

Glu  Tyr  Arg  Gln  Arg  Leu  Glu  Glu  Ala  Gly  Arg  Ala  Leu  Tyr  Ser  Leu
               340                      345                      350

Gly  Ser  Lys  Glu  Asp  Thr  Ile  Leu  Gly  Pro
          355                      360
```

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (primer)

( i x ) FEATURE:
        ( A ) NAME/KEY: misc_feature
        ( B ) LOCATION: 1..21
        ( D ) OTHER INFORMATION: /note="corresponding to bases
            69-89 of the rat brain sequence"

( x i ) SEQUENCE DESCRIPTION: SEQ ID NO:3:

CTGAGTGCGG CTGGTGATAC C                                          21

( 2 ) INFORMATION FOR SEQ ID NO:4:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (primer)

( i x ) FEATURE:
        ( A ) NAME/KEY: misc_feature
        ( B ) LOCATION: 1..48
        ( D ) OTHER INFORMATION: /note="complementary to bases
            134-181 of the rat brain sequence."

( x i ) SEQUENCE DESCRIPTION: SEQ ID NO:4:

TCTATGGCTT CCAAGTCACC CATCTGGGCC AACTGCCGGT GTATCTTC          48

( 2 ) INFORMATION FOR SEQ ID NO:5:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (primer)

( i x ) FEATURE:
        ( A ) NAME/KEY: misc_feature
        ( B ) LOCATION: 1..38
        ( D ) OTHER INFORMATION: /note="corresponding to bases 27-50
            of the rat brain sequence"

( x i ) SEQUENCE DESCRIPTION: SEQ ID NO:5:

ACGTACGTGG ATCCATGGGT GGGGGCCTGA TTGAGAGG                    38

( 2 ) INFORMATION FOR SEQ ID NO:6:

( i ) SEQUENCE CHARACTERISTICS:
   ( A ) LENGTH: 34 base pairs
   ( B ) TYPE: nucleic acid
   ( C ) STRANDEDNESS: single
   ( D ) TOPOLOGY: linear ( i i ) MOLECULE TYPE: DNA (primer)

( i x ) FEATURE:
   ( A ) NAME/KEY: misc_feature
   ( B ) LOCATION: 1..34
   ( D ) OTHER INFORMATION: /note="complementary to bases 1097-1115 of the rat brain sequence"

( x i ) SEQUENCE DESCRIPTION: SEQ ID NO:6:

ACGTACGTGA ATTCCCTAGG GACCTAGTAT AGTG    34

( 2 ) INFORMATION FOR SEQ ID NO:7:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: DNA (primer)

( i x ) FEATURE:
      ( A ) NAME/KEY: misc_feature
      ( B ) LOCATION: 1..18
      ( D ) OTHER INFORMATION: /note="complementary to bases 360-377 of the rat brain sequence"

( x i ) SEQUENCE DESCRIPTION: SEQ ID NO:7:

GGGGTCCAGC TGCATGGC    18

( 2 ) INFORMATION FOR SEQ ID NO:8:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: DNA (primer)

( i x ) FEATURE:
      ( A ) NAME/KEY: misc_feature
      ( B ) LOCATION: 1..18
      ( D ) OTHER INFORMATION: /note="corresponding to bases 299-316 of the rat brain sequence"

( x i ) SEQUENCE DESCRIPTION: SEQ ID NO:8:

TTACCGGGAC TGCATGGG    18

( 2 ) INFORMATION FOR SEQ ID NO:9:

( i ) SEQUENCE CHARACTERISTICS:
      ( A ) LENGTH: 1103 base pairs
      ( B ) TYPE: nucleic acid
      ( C ) STRANDEDNESS: single
      ( D ) TOPOLOGY: linear ( i i ) MOLECULE TYPE: cDNA ( i x ) FEATURE:
      ( A ) NAME/KEY: CDS
      ( B ) LOCATION: 10..1095

( x i ) SEQUENCE DESCRIPTION: SEQ ID NO:9:

AAGCTCAGC ATG GGT GGG GGG CTG ATT GAG AGG TAT GTG GCT GCC ATG    48
          Met Gly Gly Gly Leu Ile Glu Arg Tyr Val Ala Ala Met
           1           5                  10

| | | | | | | | | | | | | | | | | |
|---|---|---|---|---|---|---|---|---|---|---|---|---|---|---|---|---|
| GTG | CTG | AGC | GCG | GCT | GGA | GAT | ACC | TTG | GGC | TAC | TTC | AAC | GGG | AAG | TGG | 96 |
| Val | Leu | Ser | Ala | Ala | Gly | Asp | Thr | Leu | Gly | Tyr | Phe | Asn | Gly | Lys | Trp | |
| | 15 | | | | 20 | | | | | 25 | | | | | | |
| GAG | TTC | ATT | CGG | GAT | GGG | GAG | ACG | ATA | CAC | CAG | CAG | TTG | GCC | CAG | ATG | 144 |
| Glu | Phe | Ile | Arg | Asp | Gly | Glu | Thr | Ile | His | Gln | Gln | Leu | Ala | Gln | Met | |
| 30 | | | | | 35 | | | | | 40 | | | | | 45 | |
| GGT | GAC | TTG | GAA | GCC | ATA | GAT | GTG | GCA | CGA | TGG | AGA | GTC | AGT | GAT | GAT | 192 |
| Gly | Asp | Leu | Glu | Ala | Ile | Asp | Val | Ala | Arg | Trp | Arg | Val | Ser | Asp | Asp | |
| | | | | 50 | | | | | 55 | | | | | 60 | | |
| ACC | GTC | ATG | CAC | CTG | GCC | ACA | GCG | GAG | GCC | CTC | ATG | GAA | GCC | GGC | CAG | 240 |
| Thr | Val | Met | His | Leu | Ala | Thr | Ala | Glu | Ala | Leu | Met | Glu | Ala | Gly | Gln | |
| | | | 65 | | | | | 70 | | | | | 75 | | | |
| TCC | CCG | GAT | TTG | CCT | CGG | CTG | TAT | TCC | CTA | CTA | GCC | AAA | CAT | TAC | CGG | 288 |
| Ser | Pro | Asp | Leu | Pro | Arg | Leu | Tyr | Ser | Leu | Leu | Ala | Lys | His | Tyr | Arg | |
| | | 80 | | | | | 85 | | | | | 90 | | | | |
| GAC | TGC | ATG | GGA | GAC | ATG | GAT | GGC | CGG | GCA | CCA | GGT | GGT | GCT | TGC | ATG | 336 |
| Asp | Cys | Met | Gly | Asp | Met | Asp | Gly | Arg | Ala | Pro | Gly | Gly | Ala | Cys | Met | |
| | 95 | | | | | 100 | | | | | 105 | | | | | |
| CAG | AAC | GCC | ATG | CTG | CTA | CAG | CCC | AAC | AGG | GCC | GAC | GGC | TAT | AGG | ATT | 384 |
| Gln | Asn | Ala | Met | Leu | Leu | Gln | Pro | Asn | Arg | Ala | Asp | Gly | Tyr | Arg | Ile | |
| 110 | | | | | 115 | | | | | 120 | | | | | 125 | |
| CCC | TTC | AAC | AGT | CAC | GAG | GGT | GGC | TGC | GGG | GCT | GCC | ATG | CGC | GCC | ATG | 432 |
| Pro | Phe | Asn | Ser | His | Glu | Gly | Gly | Cys | Gly | Ala | Ala | Met | Arg | Ala | Met | |
| | | | | 130 | | | | | 135 | | | | | 140 | | |
| TGC | ATC | GGG | CTG | AGG | TTC | CCC | CAC | CCC | AGC | CAA | CTG | GAT | CTG | CTG | ATC | 480 |
| Cys | Ile | Gly | Leu | Arg | Phe | Pro | His | Pro | Ser | Gln | Leu | Asp | Leu | Leu | Ile | |
| | | | 145 | | | | | 150 | | | | | 155 | | | |
| CAA | GTG | AGC | ATC | GAG | AGC | GGC | CGG | ATG | ACC | CAC | CAC | CAC | CCC | ACG | GGC | 528 |
| Gln | Val | Ser | Ile | Glu | Ser | Gly | Arg | Met | Thr | His | His | His | Pro | Thr | Gly | |
| | | 160 | | | | | 165 | | | | | 170 | | | | |
| TAC | CTC | GGC | AGC | CTT | GCG | TCC | GCT | CTT | TTT | ACG | GCA | TAT | GCC | GTG | AAT | 576 |
| Tyr | Leu | Gly | Ser | Leu | Ala | Ser | Ala | Leu | Phe | Thr | Ala | Tyr | Ala | Val | Asn | |
| | 175 | | | | | 180 | | | | | 185 | | | | | |
| GGC | AAG | TCA | CCA | TGG | CAG | TGG | GGA | AAA | GGG | CTA | ATG | GAG | GTG | CTG | CCT | 624 |
| Gly | Lys | Ser | Pro | Trp | Gln | Trp | Gly | Lys | Gly | Leu | Met | Glu | Val | Leu | Pro | |
| 190 | | | | | 195 | | | | | 200 | | | | | 205 | |
| GAA | GCC | AAA | AAG | TAC | ATC | ACT | CAG | TCA | GGC | TAC | TTT | GTG | AAG | GAG | AAT | 672 |
| Glu | Ala | Lys | Lys | Tyr | Ile | Thr | Gln | Ser | Gly | Tyr | Phe | Val | Lys | Glu | Asn | |
| | | | | 210 | | | | | 215 | | | | | 220 | | |
| CTT | CAA | CAC | TGG | TCC | TAC | TTC | GAG | AAA | GAA | TGG | GAA | AAG | TAC | CTG | GAG | 720 |
| Leu | Gln | His | Trp | Ser | Tyr | Phe | Glu | Lys | Glu | Trp | Glu | Lys | Tyr | Leu | Glu | |
| | | | 225 | | | | | 230 | | | | | 235 | | | |
| CTT | AGA | GGA | ATT | TTG | GAC | GGC | AAC | TCG | GCT | CCC | GTC | TTC | CCG | CAG | CCC | 768 |
| Leu | Arg | Gly | Ile | Leu | Asp | Gly | Asn | Ser | Ala | Pro | Val | Phe | Pro | Gln | Pro | |
| | | 240 | | | | | 245 | | | | | 250 | | | | |
| TTT | GGT | GTG | AAG | GAA | AGG | GAT | CAG | TTC | TAC | ATC | GAC | GTG | AGC | TAC | TCG | 816 |
| Phe | Gly | Val | Lys | Glu | Arg | Asp | Gln | Phe | Tyr | Ile | Asp | Val | Ser | Tyr | Ser | |
| | 255 | | | | | 260 | | | | | 265 | | | | | |
| GGC | TGG | GGT | GGC | AGC | AGC | GGA | CAC | GAT | GCC | CCC | ATG | ATT | GCC | TAC | GAT | 864 |
| Gly | Trp | Gly | Gly | Ser | Ser | Gly | His | Asp | Ala | Pro | Met | Ile | Ala | Tyr | Asp | |
| 270 | | | | | 275 | | | | | 280 | | | | | 285 | |
| GCC | CTC | CTG | GCC | GCG | GGG | GAT | TCC | TGG | AAG | GAG | CTC | GCA | CAC | AGA | GCC | 912 |
| Ala | Leu | Leu | Ala | Ala | Gly | Asp | Ser | Trp | Lys | Glu | Leu | Ala | His | Arg | Ala | |
| | | | | 290 | | | | | 295 | | | | | 300 | | |
| TTC | TTC | CAC | GGT | GGA | GAC | AGT | GAT | TCC | ACG | GCC | GCC | ATT | GCT | GGC | TGC | 960 |
| Phe | Phe | His | Gly | Gly | Asp | Ser | Asp | Ser | Thr | Ala | Ala | Ile | Ala | Gly | Cys | |
| | | | 305 | | | | | 310 | | | | | 315 | | | |
| TGG | TGG | GGA | GTT | ATG | TAC | GGC | TTT | AAA | GGC | GTA | AAT | CCC | GCC | AAC | TAC | 1008 |
| Trp | Trp | Gly | Val | Met | Tyr | Gly | Phe | Lys | Gly | Val | Asn | Pro | Ala | Asn | Tyr | |
| | | 320 | | | | | 325 | | | | | 330 | | | | |

```
GAG  AAG  CTC  GAA  TAC  CGA  CAG  CGG  CTA  GAA  GAG  GCC  GGA  AGA  GCT  TTG      1056
Glu  Lys  Leu  Glu  Tyr  Arg  Gln  Arg  Leu  Glu  Glu  Ala  Gly  Arg  Ala  Leu
     335                 340                      345

TAT  TCT  CTC  GGG  TCA  AAA  GAA  GAC  CCT  GTA  TTA  GAT  CCC  TAGGGAGA            1103
Tyr  Ser  Leu  Gly  Ser  Lys  Glu  Asp  Pro  Val  Leu  Asp  Pro
350                      355                      360
```

( 2 ) INFORMATION FOR SEQ ID NO:10:

( i ) SEQUENCE CHARACTERISTICS:
        ( A ) LENGTH: 362 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Met  Gly  Gly  Gly  Leu  Ile  Glu  Arg  Tyr  Val  Ala  Ala  Met  Val  Leu  Ser
 1                       5                    10                      15

Ala  Ala  Gly  Asp  Thr  Leu  Gly  Tyr  Phe  Asn  Gly  Lys  Trp  Glu  Phe  Ile
               20                   25                      30

Arg  Asp  Gly  Glu  Thr  Ile  His  Gln  Gln  Leu  Ala  Gln  Met  Gly  Asp  Leu
          35                        40                      45

Glu  Ala  Ile  Asp  Val  Ala  Arg  Trp  Arg  Val  Ser  Asp  Thr  Val  Met
     50                        55                      60

His  Leu  Ala  Thr  Ala  Glu  Ala  Leu  Met  Glu  Ala  Gly  Gln  Ser  Pro  Asp
65                       70                   75                           80

Leu  Pro  Arg  Leu  Tyr  Ser  Leu  Leu  Ala  Lys  His  Tyr  Arg  Asp  Cys  Met
               85                        90                           95

Gly  Asp  Met  Asp  Gly  Arg  Ala  Pro  Gly  Gly  Ala  Cys  Met  Gln  Asn  Ala
              100                      105                      110

Met  Leu  Leu  Gln  Pro  Asn  Arg  Ala  Asp  Gly  Tyr  Arg  Ile  Pro  Phe  Asn
          115                      120                      125

Ser  His  Glu  Gly  Gly  Cys  Gly  Ala  Ala  Met  Arg  Ala  Met  Cys  Ile  Gly
     130                      135                      140

Leu  Arg  Phe  Pro  His  Pro  Ser  Gln  Leu  Asp  Leu  Leu  Ile  Gln  Val  Ser
145                      150                      155                     160

Ile  Glu  Ser  Gly  Arg  Met  Thr  His  His  His  Pro  Thr  Gly  Tyr  Leu  Gly
                    165                      170                      175

Ser  Leu  Ala  Ser  Ala  Leu  Phe  Thr  Ala  Tyr  Ala  Val  Asn  Gly  Lys  Ser
               180                      185                      190

Pro  Trp  Gln  Trp  Gly  Lys  Gly  Leu  Met  Glu  Val  Leu  Pro  Glu  Ala  Lys
          195                      200                      205

Lys  Tyr  Ile  Thr  Gln  Ser  Gly  Tyr  Phe  Val  Lys  Glu  Asn  Leu  Gln  His
     210                      215                      220

Trp  Ser  Tyr  Phe  Glu  Lys  Glu  Trp  Glu  Lys  Tyr  Leu  Glu  Leu  Arg  Gly
225                      230                      235                     240

Ile  Leu  Asp  Gly  Asn  Ser  Ala  Pro  Val  Phe  Pro  Gln  Pro  Phe  Gly  Val
                    245                      250                      255

Lys  Glu  Arg  Asp  Gln  Phe  Tyr  Ile  Asp  Val  Ser  Tyr  Ser  Gly  Trp  Gly
               260                      265                      270

Gly  Ser  Ser  Gly  His  Asp  Ala  Pro  Met  Ile  Ala  Tyr  Asp  Ala  Leu  Leu
          275                      280                      285

Ala  Ala  Gly  Asp  Ser  Trp  Lys  Glu  Leu  Ala  His  Arg  Ala  Phe  Phe  His
     290                      295                      300

Gly  Gly  Asp  Ser  Asp  Ser  Thr  Ala  Ala  Ile  Ala  Gly  Cys  Trp  Trp  Gly
305                      310                      315                     320
```

```
Val  Met  Tyr  Gly  Phe  Lys  Gly  Val  Asn  Pro  Ala  Asn  Tyr  Glu  Lys  Leu
               325                      330                      335

Glu  Tyr  Arg  Gln  Arg  Leu  Glu  Glu  Ala  Gly  Arg  Ala  Leu  Tyr  Ser  Leu
               340                      345                      350

Gly  Ser  Lys  Glu  Asp  Pro  Val  Leu  Asp  Pro
               355                      360
```

( 2 ) INFORMATION FOR SEQ ID NO:11:

( i ) SEQUENCE CHARACTERISTICS:
    ( A ) LENGTH: 1109 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 4..1038

( i x ) FEATURE:
    ( A ) NAME/KEY: misc_feature
    ( B ) LOCATION: 338..339
    ( D ) OTHER INFORMATION: /note="Nucleotide at position 338
          may be either G or A, and the amino acid encoded
          by this codon is either serine or asparagine."

( x i ) SEQUENCE DESCRIPTION: SEQ ID NO:11:

```
CCA  GCT  GGA  GAT  GCC  CTG  GGG  TAC  TAC  AAT  GGG  AAG  TGG  GAG  TTC  CTC      48
     Ala  Gly  Asp  Ala  Leu  Gly  Tyr  Tyr  Asn  Gly  Lys  Trp  Glu  Phe  Leu
     1              5                        10                       15

CAG  GAT  GGG  GAG  AAG  ATA  CAC  CGG  CAG  TTG  GCC  CAG  CTG  GGC  GGC  TTG      96
Gln  Asp  Gly  Glu  Lys  Ile  His  Arg  Gln  Leu  Ala  Gln  Leu  Gly  Gly  Leu
                    20                       25                       30

GAT  GCC  CTA  GAC  GTG  GGA  AGG  TGG  AGA  GTT  AGT  GAC  GAC  ACA  GTG  ATG     144
Asp  Ala  Leu  Asp  Val  Gly  Arg  Trp  Arg  Val  Ser  Asp  Asp  Thr  Val  Met
               35                       40                       45

CAC  TTG  GCC  ACA  GCA  GAA  GCT  CTT  GTG  GAA  GCT  GGG  AAA  GCC  CCT  AAG     192
His  Leu  Ala  Thr  Ala  Glu  Ala  Leu  Val  Glu  Ala  Gly  Lys  Ala  Pro  Lys
          50                       55                       60

TTG  ACT  CAA  CTG  TAT  TAC  CTC  CTT  GCT  AAG  CAT  TAC  CAA  GAC  TGC  ATG     240
Leu  Thr  Gln  Leu  Tyr  Tyr  Leu  Leu  Ala  Lys  His  Tyr  Gln  Asp  Cys  Met
     65                       70                       75

GAA  GAC  ATG  GAT  GGG  CGG  GCA  CCA  GGT  GGT  GCC  TCG  GTG  CAC  AAC  GCC     288
Glu  Asp  Met  Asp  Gly  Arg  Ala  Pro  Gly  Gly  Ala  Ser  Val  His  Asn  Ala
80                       85                       90                       95

ATG  CAG  CTG  AAG  CCG  GGC  AAG  CCC  AAT  GGC  TGG  AGG  ATT  CCC  TTC  AAC     336
Met  Gln  Leu  Lys  Pro  Gly  Lys  Pro  Asn  Gly  Trp  Arg  Ile  Pro  Phe  Asn
                    100                      105                      110

AGC  CAT  GAG  GGC  GGC  TGT  GGG  GCT  GCC  ATG  CGG  GCC  ATG  TGC  ATC  GGT     384
Ser  His  Glu  Gly  Gly  Cys  Gly  Ala  Ala  Met  Arg  Ala  Met  Cys  Ile  Gly
               115                      120                      125

CTC  AGG  TTC  CCA  CAC  CAT  AGC  CAA  CTG  GAC  ACA  CTG  ATC  CAA  GTG  AGC     432
Leu  Arg  Phe  Pro  His  His  Ser  Gln  Leu  Asp  Thr  Leu  Ile  Gln  Val  Ser
          130                      135                      140

ATC  GAG  AGT  GGT  CGG  ATG  ACC  CAC  CAC  CAC  CCA  ACA  GGC  TAC  CTG  GGG     480
Ile  Glu  Ser  Gly  Arg  Met  Thr  His  His  His  Pro  Thr  Gly  Tyr  Leu  Gly
     145                      150                      155

GCC  CTT  GCG  TCT  GCT  CTT  TTT  ACA  GCC  TAT  GCT  GTG  AAT  AGC  AGA  CCA     528
Ala  Leu  Ala  Ser  Ala  Leu  Phe  Thr  Ala  Tyr  Ala  Val  Asn  Ser  Arg  Pro
160                      165                      170                      175

CCC  TTG  CAG  TGG  GGA  AAA  GGA  CTG  ATG  GAG  CTG  CTA  CCA  GAA  GCT  AAA     576
Pro  Leu  Gln  Trp  Gly  Lys  Gly  Leu  Met  Glu  Leu  Leu  Pro  Glu  Ala  Lys
```

-continued

```
                        180                           185                             190
AAG  TAC  ATT  GTC  CAA  TCA  GGC  TAC  TTT  GTA  GAG  GAA  AAT  CTT  CAA  CAC           624
Lys  Tyr  Ile  Val  Gln  Ser  Gly  Tyr  Phe  Val  Glu  Glu  Asn  Leu  Gln  His
               195                      200                      205

TGG  TCC  TAC  TTC  CAA  ACC  AAA  TGG  GAA  AAT  TAC  CTA  AAA  CTT  AGA  GGG           672
Trp  Ser  Tyr  Phe  Gln  Thr  Lys  Trp  Glu  Asn  Tyr  Leu  Lys  Leu  Arg  Gly
               210                      215                      220

ATT  TTG  GAT  GGA  GAA  TCA  GCC  CCT  ACC  TTC  CCT  GAG  TCT  TTC  GGT  GTG           720
Ile  Leu  Asp  Gly  Glu  Ser  Ala  Pro  Thr  Phe  Pro  Glu  Ser  Phe  Gly  Val
               225                      230                      235

AAG  GAG  AGG  GAT  CAG  TTC  TAC  ACC  TCC  CTG  AGC  TAC  TCT  GGC  TGG  GGT           768
Lys  Glu  Arg  Asp  Gln  Phe  Tyr  Thr  Ser  Leu  Ser  Tyr  Ser  Gly  Trp  Gly
240                      245                      250                      255

GGC  AGC  AGT  GGG  CAC  GAT  GCC  CCC  ATG  ATT  GCC  TAC  GAT  GCT  GTT  CTT           816
Gly  Ser  Ser  Gly  His  Asp  Ala  Pro  Met  Ile  Ala  Tyr  Asp  Ala  Val  Leu
               260                      265                      270

GCT  GCA  GGA  GAC  TCC  TGG  AAG  GAG  CTT  GCC  CAC  CGA  GCC  TTT  TTC  CAT           864
Ala  Ala  Gly  Asp  Ser  Trp  Lys  Glu  Leu  Ala  His  Arg  Ala  Phe  Phe  His
               275                      280                      285

GGT  GGA  GAC  AGT  GAT  TCT  ACA  GCT  GCC  ATT  GCT  GGC  TGC  TGG  TGG  GGA           912
Gly  Gly  Asp  Ser  Asp  Ser  Thr  Ala  Ala  Ile  Ala  Gly  Cys  Trp  Trp  Gly
               290                      295                      300

GTT  ATG  TAT  GGT  TTT  AAA  GGA  GTG  AGT  CCC  TCC  AAC  TAT  GAG  AAA  CTA           960
Val  Met  Tyr  Gly  Phe  Lys  Gly  Val  Ser  Pro  Ser  Asn  Tyr  Glu  Lys  Leu
          305                      310                      315

GAA  TAC  AGA  AAC  CGG  CTG  GAA  GAG  ACA  GCT  AGG  GCT  TTA  TAT  TCT  CTC          1008
Glu  Tyr  Arg  Asn  Arg  Leu  Glu  Glu  Thr  Ala  Arg  Ala  Leu  Tyr  Ser  Leu
320                      325                      330                      335

GGG  TCA  AAA  GAA  GAC  ACT  GTA  ATT  TCC  CTT  TAGGGAGACG  TGATGTTCAC              1058
Gly  Ser  Lys  Glu  Asp  Thr  Val  Ile  Ser  Leu
               340                      345

TTCTGATGGA   TTCTTCTTTT   GTGTATTTCC   TTTTCTGCTA   TTTCTTTTCA  G                    1109
```

( 2 ) INFORMATION FOR SEQ ID NO:12:

( i ) SEQUENCE CHARACTERISTICS:
        ( A ) LENGTH: 345 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Ala  Gly  Asp  Ala  Leu  Gly  Tyr  Tyr  Asn  Gly  Lys  Trp  Glu  Phe  Leu  Gln
  1                 5                      10                      15

Asp  Gly  Glu  Lys  Ile  His  Arg  Gln  Leu  Ala  Gln  Leu  Gly  Gly  Leu  Asp
                20                      25                      30

Ala  Leu  Asp  Val  Gly  Arg  Trp  Arg  Val  Ser  Asp  Asp  Thr  Val  Met  His
           35                      40                      45

Leu  Ala  Thr  Ala  Glu  Ala  Leu  Val  Glu  Ala  Gly  Lys  Ala  Pro  Lys  Leu
      50                      55                      60

Thr  Gln  Leu  Tyr  Tyr  Leu  Leu  Ala  Lys  His  Tyr  Gln  Asp  Cys  Met  Glu
 65                      70                      75                      80

Asp  Met  Asp  Gly  Arg  Ala  Pro  Gly  Gly  Ala  Ser  Val  His  Asn  Ala  Met
                85                      90                      95

Gln  Leu  Lys  Pro  Gly  Lys  Pro  Asn  Gly  Trp  Arg  Ile  Pro  Phe  Asn  Ser
          100                     105                     110

His  Glu  Gly  Gly  Cys  Gly  Ala  Ala  Met  Arg  Ala  Met  Cys  Ile  Gly  Leu
           115                     120                     125
```

| | | | | | | | | | | | | | | | |
|---|---|---|---|---|---|---|---|---|---|---|---|---|---|---|---|
| Arg | Phe 130 | Pro | His | His | Ser | Gln 135 | Leu | Asp | Thr | Leu | Ile 140 | Gln | Val | Ser | Ile |
| Glu 145 | Ser | Gly | Arg | Met | Thr 150 | His | His | His | Pro | Thr 155 | Gly | Tyr | Leu | Gly | Ala 160 |
| Leu | Ala | Ser | Ala | Leu 165 | Phe | Thr | Ala | Tyr | Ala 170 | Val | Asn | Ser | Arg | Pro 175 | Pro |
| Leu | Gln | Trp | Gly 180 | Lys | Gly | Leu | Met | Glu 185 | Leu | Leu | Pro | Glu | Ala 190 | Lys | Lys |
| Tyr | Ile | Val 195 | Gln | Ser | Gly | Tyr | Phe 200 | Val | Glu | Glu | Asn | Leu 205 | Gln | His | Trp |
| Ser | Tyr 210 | Phe | Gln | Thr | Lys | Trp 215 | Glu | Asn | Tyr | Leu | Lys 220 | Leu | Arg | Gly | Ile |
| Leu 225 | Asp | Gly | Glu | Ser | Ala 230 | Pro | Thr | Phe | Pro | Glu 235 | Ser | Phe | Gly | Val | Lys 240 |
| Glu | Arg | Asp | Gln | Phe 245 | Tyr | Thr | Ser | Leu | Ser 250 | Tyr | Ser | Gly | Trp | Gly 255 | Gly |
| Ser | Ser | Gly | His 260 | Asp | Ala | Pro | Met | Ile 265 | Ala | Tyr | Asp | Ala | Val 270 | Leu | Ala |
| Ala | Gly | Asp 275 | Ser | Trp | Lys | Glu | Leu 280 | Ala | His | Arg | Ala | Phe 285 | Phe | His | Gly |
| Gly | Asp 290 | Ser | Asp | Ser | Thr | Ala 295 | Ala | Ile | Ala | Gly | Cys 300 | Trp | Trp | Gly | Val |
| Met 305 | Tyr | Gly | Phe | Lys | Gly 310 | Val | Ser | Pro | Ser | Asn 315 | Tyr | Glu | Lys | Leu | Glu 320 |
| Tyr | Arg | Asn | Arg | Leu 325 | Glu | Glu | Thr | Ala | Arg 330 | Ala | Leu | Tyr | Ser | Leu 335 | Gly |
| Ser | Lys | Glu | Asp 340 | Thr | Val | Ile | Ser | Leu 345 | | | | | | | |

CLONES ENCODING MAMMALIAN ADP-RIBOSYLARGININE HYDROLASES

This is a division of application Ser. No. 07/888,231 filed May 22, 1992, now abandoned.

BACKGROUND OF THE INVENTION

Field of the Invention

The present invention relates to the production of mammalian ADP-ribosylarginine hydrolases. These enzymes can be manufactured using recombinant DNA technology and are useful in regulation of proteins involved in key metabolic pathways.

ADP-ribosylarginine hydrolases are enzymes involved in the reversible modification of regulatory proteins. They are found in a variety of mammalian tissues and are useful for altering the toxicity of bacterial toxins and activity of endogenous mammalian enzymes which exert their effect by transferring ADP-ribose to an arginine residue of the regulatory proteins.

SUMMARY OF THE INVENTION

This invention provides for a substantially purified, recombinantly produced mammalian ADP-ribosylarginine hydrolase, wherein the hydrolase binds to a polyclonal antibody specific for the hydrolase of Seq. I.D. No. 2. Such proteins are substantially free of contaminating biological material found in the cells which naturally produce the hydrolase. Preferred mammalian sources include: (a) humans; (b) rats; and (c) mice.

This invention further provides for isolated nucleic acid comprising a sequence encoding a mammalian ADP-ribosylarginine hydrolase as described above. The isolated nucleic acid can be part of a replication vector or an expression vector. The vectors are preferably plasmids. A preferred gene encodes the rat hydrolase as depicted in Seq. I.D. No. 2. The gene can be interrupted (genomic) or uninterrupted (e.g., cDNA).

The preferred host cells for producing the hydrolases of this invention are bacterial cells and mammalian cells.

This invention further provides for a method of isolating from mammalian tissue a DNA sequence encoding ADP-ribosylarginine hydrolase said method comprising, probing a DNA library or cDNA pool prepared from mammalian tissue with an oligonucleotide which binds to a conserved portion of the nucleic acid of the rat brain ADP-ribosylarginine hydrolase cDNA within bases 418 to 912 of Seq. I.D. No 1 (with A of ATG equal to 1), and wherein said oligonucleotide is able to detect cDNA encoding ADP-ribosylarginine hydrolase with less than 1% false positives during the probing of the library or pool. This method is preferably applicable to rat, mouse and human tissue.

DETAILED DESCRIPTION

A. Definitions

A1. Proteins.

The terms "peptide", "polypeptide" or "protein" are used interchangeably herein. The term "substantial identity", when referring to polypeptides, indicates that the polypeptide or protein in question is at least about 70% identical to an entire naturally occurring protein (native) or a portion thereof, and preferably at least about 95% identical.

As used herein, the terms "isolated" and "substantially pure" are used interchangeably and describe a protein that has been separated from components which naturally accompany it. Typically, a monomeric protein is substantially pure when at least about 60 to 75% of a sample exhibits a single polypeptide backbone. Minor variants or chemical modifications typically share the same polypeptide sequence. A substantially purified protein will typically comprise over about 85 to 90% of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band on a polyacrylamide gel upon staining. For certain purposes high resolution will be needed and HPLC or a similar means for purification be utilized.

A polypeptide is substantially free of naturally-associated components when it is separated from the native contaminants which accompany it in its natural state. Thus, a polypeptide which is chemically synthesized or synthesized in a cellular system different from the cell from which it naturally originates will be substantially free from its naturally-associated components.

The proteins of this invention may be purified to substantial homogeneity by standard techniques well known in the art, including selective precipitation with such substances as ammonium sulfate, column chromatography, immunopurification methods, and others. See, for instance, R. Scopes, *Protein Purification: Principles and Practice*, Springer-Verlag: New York (1982), incorporated herein by reference.

A2. Nucleic acids.

The phrase "nucleic acid sequence" refers to a single or double-stranded polymer of deoxyribonucleotide or ribonucleotide bases read from the 5' to the 3' end. It includes both self-replicating plasmids, infectious polymers of DNA or RNA and non-functional DNA or RNA.

Nucleic acids, as used herein, may be DNA or RNA. Additionally, substantial nucleic acid sequence identity exists when a nucleic acid segment will hybridize under selective hybridization conditions, to a complement of another nucleic acid strand.

The term "complementary" means that one nucleic acid is identical to, or hybridizes selectively to, another nucleic acid. Selectivity of hybridization exists when hybridization occurs that is more selective than total lack of specificity. Typically, selective hybridization will occur when there is at least about 55% identity over a stretch of at least 14–25 nucleotides, preferably at least about 65%, more preferably at least about 75%, and most preferably at least about 90%. See, M. Kanehisa *Nucleic Acids Res.* 12:203 (1984), incorporated herein by reference.

"Isolated" or "substantially pure", when referring to nucleic acids, refer to those that have been purified away from other cellular components or other contaminants, e.g., other cellular nucleic acids or proteins, by standard techniques, including alkaline/SDS treatment, CsCl banding, column chromatography, and others well known in the art. See, F. Ausubel, et al., ed. *Current Protocols in Molecular Biology*, Greene Publishing and Wiley-Interscience, New York (1987), incorporated herein by reference.

"Oligonucleotides" may be synthetic DNA fragments prepared, for example, by the phosphoramidite method described by Beaucage and Carruthers, *Tetra. Letts.* 22:1859–1862 (1981), or by the triester method according to Matteucci, et al., *J. Am. Chem. Soc.*, 103:3185 (1981), both incorporated herein by reference. A double stranded fragment may then be obtained, if desired, by annealing the chemically synthesized single strands together under appropriate conditions or by synthesizing the complementary strand using DNA polymerase with an appropriate primer sequence.

An oligonucleotide is complementary to a target nucleic acid when it will anneal only to a single desired position on that target nucleic acid under conditions determined as described below. Proper annealing conditions depend, for example, upon an oligonucleotide's length, base composition, and the number of mismatches and their position on an oligonucleotide, and must often be determined empirically. For discussions of oligonucleotide design and annealing conditions, see, for example, Sambrook et al., *Molecular Cloning: A Laboratory Manual* (2nd ed.), Vols. 1-3, Cold Spring Harbor Laboratory, (1989) or *Current Protocols in Molecular Biology*, F. Ausubel et al., ed. Greene Publishing and Wiley-Interscience, New York (1987), both of which are incorporated herein by reference.

The term "promoter" refers to a region of DNA upstream from the structural gene and involved in recognition and binding RNA polymerase and other proteins to initiate transcription.

A "constitutive" promoter is a promoter which is active under all environmental conditions and all states of development or cell differentiation.

An "inducible" promoter is a promoter which is under environmental or developmental control.

The term "operably linked" refers to functional linkage between a promoter and a second sequence, wherein the promoter sequence initiates transcription of RNA corresponding to the second sequence. Generally, operably linked means that the nucleic acid sequences being linked are continuous and, where necessary to join two protein coding regions, contiguous and in reading frame.

Techniques for nucleic acid manipulation, such as subcloning nucleic acid sequences encoding polypeptides into expression vectors, labelling probes, DNA hybridization, and so on are described generally, for example in Sambrook et al. (1989) op. cit., or Ausubel et al., ed. (1987) op. cit., both of which are incorporated herein by reference.

"Expression vectors", "cloning vectors", or "vectors" are often plasmids or other nucleic acid molecules that are able to replicate in a chosen host cell. Expression vectors may replicate autonomously, or they may replicate by being inserted into the genome of the host cell, by methods well known in the art. Vectors that replicate autonomously will have an origin of replication or autonomous replicating sequence (ARS) that is functional in the chosen host cell(s). Often, it is desirable for a vector to be usable in more than one host cell, e.g., in *E. coli* for cloning and construction, and in a mammalian cell for expression.

A useful, but not necessary element of an expression or other vector is one or more selectable or screenable markers.

A selectable marker may be a gene that codes for a protein necessary for the survival or growth of a host cell transformed with the vector. The presence of this gene ensures the growth of only those host cells that contain the vector. Typical selection genes encode proteins that (a) confer resistance to antibiotics or other toxic substances, e.g., ampicillin, neomycin, methotrexate, etc.; (b) complement auxotrophic deficiencies, or (c) supply critical nutrients not available from complex media, e.g., the gene encoding D-alanine racemase for Bacilli. The choice of the proper selectable marker will depend on the host cell, and appropriate markers for different hosts are well known in the art.

A screenable marker is a gene that codes for a protein whose activity is easily detected, allowing cells expressing such a marker to be readily identified. Such markers include, for example, β-galactosidase, β-glucuronidase, and luciferase.

Expression vectors contain, in addition to those elements described above, sequences for controlling expression of a gene operably linked to these control sequences. Such an expression "cassette" may contain a promoter, an enhancer and necessary processing information sites, such as ribosome-binding sites, RNA splice sites, polyadenylation sites, transcriptional terminator sequences and mRNA stabilizing sequences. Control sequences will be chosen so that the sequences are functional in the desired host cell.

For expression in prokaryotes, bacterial promoters such as the trp and lac promoters, tRNA gene promoters, promoters of genes encoding glycolytic enzyme, and bacteriophage promoters, are known and commonly used. See, Sambrook et al. (1989) op. cit., incorporated herein by reference.

For expression in mammalian or other eukaryotic cells, the enhancers or promoters may be those derived from viruses, such as SV40, adenovirus, bovine papilloma virus, mouse mammary tumor virus, avian sarcoma viruses, adenovirus II, or polyoma virus, and the like. See, *Enhancers and Eukaryotic Gene Expression*, Cold Spring Harbor Press, N.Y. (1983), incorporated herein by reference.

For expression in other systems, such as insect cell culture or yeast cells, one may use conveniently available expression vectors which include host cell compatible replication systems and expression control sequences to which the nucleic acid that codes for the polypeptide to be expressed may be operably linked. For example, the baculovirus vector system is commonly used in insect cell culture expression. Examples of workable combinations of cell lines and expression vectors are described in Sambrook et al. (1989) op. cit.; see also, Metzger et al. *Nature* 334:31 (1989), incorporated herein by reference. Suitable vectors and promoters for use in yeast expression are described in R. Hitzeman et al., EP 73,657A, incorporated herein by reference.

Expression vectors may also include secretion signals, which allow the protein to cross the cell membrane and either pass completely out of the cell permitting more convenient purification, or else lodge in cell membranes, and thus attain its functional topology.

A3. Host cells.

The term "suitable host" refers to a microorganism or cell that is compatible with a recombinant plasmid, DNA sequence or recombinant expression cassette and will permit the plasmid to replicate, to be incorporated into its genome, or to be expressed.

Hosts may include such organisms as bacteria (e.g., *E. coli* or *B. subtilis*), plant cells, insect cells, mammalian cells, yeast or filamentous fungi, among others.

The term "transformation" refers to the introduction of vectors containing the nucleic acids of interest directly into host cells by well known methods. Transformation methods, which vary depending on the type of host cell, include electroporation; transfection employing calcium chloride, rubidium chloride calcium phosphate, DEAE-dextran, or other substances; microprojectile bombardment; lipofection; infection (where the vector is an infectious agent); and other methods. See generally, Sambrook et al., (1989) op. cit. and Ausubel et al. (ed.), (1987) op. cit., both incorporated herein by reference. The cells into which have been introduced nucleic acids described above are meant to also include the progeny of such cells.

B. Description of the Invention

B1. Proteins

The present invention provides recombinantly produced, mammalian ADP-ribosylarginine hydrolases. The proteins of this invention are useful for determining the presence and stereochemical nature of ADP-ribosyl arginine linkages. Such information is helpful for persons analyzing the biological impact of ADP-ribose on proteins. The native ADP-ribosylarginine hydrolases participate in cell metabolism by modifying regulatory proteins. Additionally, ADP-ribosylarginine hydrolases may be useful for altering the toxicity of bacterial toxins upon mammalian cells (e.g., cholera toxin and endogenous mammalian enzymes that act by similar mechanisms).

The mammalian ADP-ribosylarginine hydrolases of the present invention include not only those with the identical amino acid sequences of the native enzymes but also allelic variants, naturally or synthetically produced mutants, including point, deletion, and insertion mutants. Also included are alternatively expressed variants, proteins encoded by nucleic acids that hybridize under high or low stringency conditions to nucleic acids that encode naturally occurring ADP-ribosylarginine hydrolases.

Polypeptides having amino acid sequence changes from those claimed, due to, for example, genetic variation, both natural and induced, are also included. Induced mutants may be derived from nucleic acids encoding these proteins by using irradiation or exposure to chemical mutagens such as EMS, or may take the form of engineered changes by site-specific mutagenesis or other techniques of modern molecular biology. See, e.g., Sambrook, Fritsch and Maniatis (1989), *Molecular Cloning: A Laboratory Manual* (2nd ed.), CSH Press, incorporated herein by reference.

There is a limit to the total number of amino acids that can be replaced in a protein, this limit being defined by the retention of biological activity. Biological activity is easily assayed by the methods disclosed herein.

The recombinant protein is understood to have the same characteristic biological activity of the native protein. Biological activity is the ability to hydrolyze an ADP-ribosyl moiety from a modified protein or amino acid. Additionally the recombinant hydrolase will cross-react in a Western blot with polyclonal antibodies generated against the 39 kDa rat brain ADP-ribosylarginine hydrolase having the amino acid sequence depicted in Seq. I.D. No. 2.

The polyclonal antibodies can be raised against an ADP-ribosylarginine hydrolase of Seq. I.D. No. 2 by standard techniques which are known to those skilled in the art. The antibody can be generated in rabbits or other mammals by injection of an adjuvant such as pertussis vaccine followed by a purified ADP-ribosylarginine hydrolase, and subsequent bleeding to assess the antibody titer on Western blots.

The polypeptides of the present invention may be isolated from natural sources, produced by chemical synthesis or by recombinant DNA methods.

Purification from mammalian tissue is one method used to isolate ADP-ribosylarginine hydrolase. The tissue used is preferably from brain but may also be from muscle, heart, lung, kidney, spleen, liver, or testis. The preferred mammals include humans, rats, mice, rabbits and cows. Purification follows steps known to those skilled in the art.

Briefly, tissue is homogenized with an appropriate buffer and centrifuged. The precipitate is again washed in a buffer, centrifuged, treated with a resin and filtered. The filtrate is subjected to column chromatography on a variety of supports including hydrophobic interaction supports (such as phenyl Sepharose), ionic interaction resins (e.g., DE-52), gel permeation supports (e.g., Ultrogel AcA 54), and organomercurial supports which interact with sulfhydryl groups. The columns are eluted each time with an appropriate buffer. The eluate is then assayed for ADP-ribosylarginine hydrolase using the assay provided in the example section. The desired hydrolases are purified to homogeneity by SDS-polyacrylamide gels and have approximate mobilities consistent with a 39 kDa protein.

The polypeptides of the present invention may also be produced by chemical or enzymatic synthesis. Techniques for solid phase chemical synthesis of polypeptides are described, for example, in Merrifield, J. Amer. Chem. Soc. 85:2149–2156 (1963), incorporated herein by reference. Such chemical synthesis is generally employed for the production of polypeptides of fewer than about 100 amino acids, more usually fewer than about 80 amino acids, and typically fewer than about 50 amino acids.

Alternatively and preferably, ADP-ribosylarginine hydrolase may be produced by recombinant DNA technology (described in detail below). This involves the expression in host cells of recombinant DNA molecules encoding a desired portion, whether synthetic or natural, of the ADP-ribosylarginine hydrolase.

B2. Nucleic Acids

Isolated nucleic acid sequences which encode ADP-ribosylarginine hydrolase are also described herein. It should be understood that alternative sequences could be used to express analogs of ADP-ribosylarginine hydrolase which contain amino acid substitutions, but which have biological activity characteristic of the native protein. Furthermore, due to the degeneracy of the genetic code, equivalent codons may be substituted to encode the same polypeptide sequence.

The nucleic acid compositions of this invention, whether RNA, cDNA, genomic DNA, or a hybrid of the various combinations, may be isolated from natural sources or may be synthesized in vitro. The nucleic acids claimed may be present in transformed or transfected whole cells, in a transformed or transfected cell lysate, or in a partially purified or substantially pure form.

Oligonucleotides are also included in the claimed invention. Such oligonucleotides are useful for use as probes for the presence of ADP-ribosylarginine hydrolase genes in physiological samples, and as primers for gene amplification. The oligonucleotide sequences will usually be at least about 20 nucleotides in length.

A method of isolating nucleic acid sequences which encode ADP-ribosylarginine hydrolase is also described herein. Briefly, the nucleic acid sequences can be isolated by probing a DNA library which is comprised of either genomic DNA or cDNA. Libraries may be either from commercial sources or prepared from mammalian tissue by techniques known to those skilled in the art. The preferred cDNA libraries are human brain and rat brain cDNA libraries which are available from commercial sources.

The DNA libraries can be probed by plaque hybridization using oligonucleotide probes of at least 20 base pairs which are complementary to conserved sequences of the genes encoding ADP-ribosylarginine hydrolases. The preferred probes are the intact cDNA of humans, rats or mice which encode ADP-ribosylarginine hydrolase, or conserved portions thereof. Additionally, the probes are labeled to facilitate isolation of the hybridized clones. Labeling can be by any of the techniques known to those skilled in the art, but typically the probes are labeled with $^{32}$P using terminal deoxynucleotidyltransferase. If the nucleic acid sequence isolated from the DNA library is not an intact gene, a cDNA encompassing the complete hydrolase coding region can be prepared by a series of three polymerase chain reactions (PCRs) which amplify and join clones by overlap extensions. Alternatively and preferably the DNA encoding the enzyme can be obtained using PCR.

The polymerase chain reaction (PCR) or other in vitro amplification methods are useful for isolating the genes encoding ADP-ribosylarginine hydrolase from physiological samples. The sequence of PCR primers, as for probes, may be based on either conserved or variable regions of the ADP-ribosylarginine hydrolase gene, for purposes discussed above, or may be based upon any other claimed nucleic acid. Exact complementarity to the nucleic acids being tested for is not required, but rather substantial complementarity is sufficient.

Using the sequences provided herein, those of skill may use polymerase chain reaction technology (PCR) to amplify nucleic acid encoding ADP-ribosylarginine hydrolase directly from mRNA extractions, from cDNA, from genomic libraries or cDNA libraries. Polymerase chain reaction (PCR) or other in vitro amplification methods may also be useful, for example, to clone nucleic acid sequences that code for proteins to be expressed, to make nucleic acids to use as probes for detecting the presence of ADP-ribosylarginine hydrolase in physiological samples, for nucleic acid sequencing, or for other purposes. Appropriate primers and probes for identifying ADP-ribosylarginine hydrolase from alternative mammalian tissues are generated from comparisons of the sequences provided herein. Examples 4 and 5 provide illustrative steps for such work. Therein, PCR was used to isolate the nucleic acid sequences encoding the mouse and human hydrolases. For a general overview of PCR see *PCR Protocols: A Guide to Methods and Applications*. (Innis, M, Gelfand, D., Shinsky, J. and White, T., eds.), Academic Press, San Diego (1990), incorporated herein by reference.

B3. Production of ADP-ribosylarginine hydrolase by Recombinant DNA Technology

Through the use of recombinant DNA techniques one may express ADP-ribosylarginine hydrolase in yeast, filamentous fungal, insect (especially employing baculoviral vectors), mammalian cells, and preferably in bacterial systems. For this purpose, the natural or synthetic nucleic acids included in the invention will typically be operably linked to a promoter (which is either constitutive or inducible), and may be incorporated into an expression vector.

The isolated nucleic acid sequences encoding ADP-ribosylarginine hydrolase can then be inserted into a cloning vector suitable for replication and integration in either prokaryotes or eukaryotes. The cloning vectors contain transcription and translation terminators, initiation sequences, and promoters useful for regulation of the expression of ADP-ribosylarginine hydrolases. The vectors are comprised of expression cassettes containing at least one independent terminator sequence, sequences permitting replication of the plasmid in both eukaryotes and prokaryotes, i.e., shuttle vectors, and selection markers for both prokaryotic and eukaryotic systems. It is understood that the cloning vectors include those which directly express the hydrolase and those which are capable of expressing fusion proteins comprised of an ADP-ribosylarginine hydrolase signal peptide fused to any foreign gene. In the described embodiment of this invention pGEX-2T is used as a vector for the subcloning and amplification of desired gene sequences.

Methods for the expression of cloned genes in bacteria are well known. To obtain high level expression of a cloned gene in a prokaryotic system, it is essential to construct expression vectors which contain, at a minimum, a strong promoter to direct mRNA transcription termination. The inclusion of selection markers in DNA vectors transformed in *E. coli* is also useful. Examples of such markers include genes specifying resistance to ampicillin, tetracycline, or chloramphenicol. See Sambrook for details concerning selection markers and promoters for use in *E. coli*.

It is expected that those of skill in the art are knowledgeable in the expression systems chosen for expression of the desired ADP-ribosylarginine hydrolase and no attempt to describe in detail the various methods known for the expression of proteins in eukaryotes will be made.

Suitable hosts may include plant cells, insect cells, mammalian cells, yeast, filamentous fungi, or preferably, bacteria (e.g., *E. coli* or *B. subtilis*).

Proteins produced by recombinant DNA technology may be purified by the techniques described above for the natural protein. Alternatively and preferably, fusion proteins produced by the above method may be purified by a combination of sonication and affinity chromatography. Subsequent digestion of the fusion protein with an appropriate proteolytic enzyme releases the desired ADP-ribosylarginine hydrolase.

In summary, cloned cDNA encoding ADP-ribosylarginine hydrolase can prepared by probing or amplifying select regions of a mixed cDNA or genomic pool using the probes and primers generated from the sequences provided herein or by purifying the protein (hydrolase) from rat brain and other mammalian tissues and determining portions of the protein amino acid sequence, constructing degenerate oligonucleotide probes corresponding to the amino acid sequence and screening an appropriate mammalian cDNA library.

Briefly, the manipulations to prepare ADP-ribosylarginine hydrolase cDNA and introduce it into *E. coli* involve 1) isolating mRNA from mammalian brain, 2) preparing cDNA from the mRNA, or in the alternative to 1) and 2), using a commercial cDNA library, 3) screening the cDNA for the desired sequence, 4) linking a promoter to the desired cDNA, 5) transforming suitable host cells, and 6) selecting and regenerating cells which contain the desired gene sequence.

The following experimental results are offered by way of example and not by way of limitation.

EXAMPLE 1

Rat Brain ADP-ribosylarginine hydrolase

A. Purification

To obtain rat brain ADP-ribosylarginine hydrolase, frozen rat brains (318 gm) were homogenized (two 1-min pulses) in 2 l of 10 mM potassium phospyhate, pH 7.5/1 mM EDTA in a Waring Blender. The homogenate (2.2 l) was centrifuged at 17,000 xg for 1 h. The precipitate was washed once in homogenization buffer (1 l) and centrifuged at 17,000 xg for 1 h. The supernatant and wash were combined (2720 ml) and mixed with DE-52 (2.5 l) for 90 min at 4° C.

The resin was transferred to a funnel, washed with 10 mM potassium phosphate, pH 7.5/1 mM EDTA (10 l) and eluted with 0.3M NaCl/20 mM potassium phosphate, pH 7.5/1 mM EDTA (3.1 l). After adding 420 ml of 4M NaCl, the DE-52 eluate was applied to phenyl Sepharose (13.5 cm×4.9 cm), washed first with 0.3M NaCl/20 mM potassium phosphate, pH 7.5/1 mM EDTA (2 l) and then with 40 mM potassium phosphate, pH 7.5/1 mM EDTA (1 l), followed by elution with 50% ethylene glycol/40 mM potassium phosphate, pH 7.5/1 mM EDTA (1140 ml).

The eluate was mixed with an equal volume of water and applied to a column (2.5×40 cm) of DE-52 equilibrated with 10 mM potassium phosphate, pH 7.5/1 mM EDTA/20% ethylene glycol which was eluted with a linear gradient of 0 to 300 mM NaCl in 20% ethylene glycol/10 mM potassium phosphate, pH 7.5/1 mM EDTA (300 ml/300 ml).

The active fractions (127 ml, as assayed by the method in part C infra) were applied to a column (2.5×36 cm) of hydroxylapatite which was eluted with a linear gradient of 10 mM to 250 mM potassium phosphate, pH 7.5 in 20% ethylene glycol/0.1M NaCl/1 mM EDTA (300 ml/300 ml). The active fractions (108 ml) were applied to a column (0.5×10 cm) of Affi-Gel 501 organo-mercurial agarose, which was washed with 20 mM potassium phosphate, pH 7.5/20% ethylene glycol/0.1M NaCl/1 mM EDTA and eluted with 20 mM potassium phosphate, pH 7.5/0.1M NaCl/5 mM dithiothreitol/20% ethylene glycol/1 mM EDTA. The eluate (8 ml) was applied to a column (1.2×90 cm) of Ultrogel AcA 54, which had been equilibrated with 20% ethylene glycol/0.1M NaCl/20 mM potassium phosphate, pH 7.5/1 mM EDTA. Active fractions were concentrated in a Centriprep Concentrator (14.5 ml to 1.5 ml) and chromatographed again on Ultrogel AcA 54 as before. The purified rat brain hydrolase exhibited one major band on SDS-polyacrylamide gels, which had a mobility consistent with a 39 kDa protein.

B. Amino acid Sequencing of rat brain ADP-ribosylarginine hydrolase

The protein sequence of the purified hydrolase was obtained from HPLC-purified tryptic fragments by Harvard Microchem (Cambridge, Mass.). To isolate CNBr fragments, the purified hydrolase (~100 µg) was cleaved with 50 µl of 10% CNBr in 50% formic acid overnight at 37° C. After 10X dilution with HPLC grade water, the mixture was lyophilized, dissolved in 0.1% trifluoroacetic acid (TFA) in 10% $CH_3CN$, and subjected to reverse-phase HPLC on a Vydac $C_4$ column (214TP54, particle size 5µ, 0.45×25 cm). The elution was performed at 0.5 ml/min with a $CH_3CN$ gradient (solvent A=0.1% TFA in water, solvent B=0.1% TFA, 70% $CH_3CN$ in water) programmed as follows: t=0 min, B=13%; t=25, B=50; t=50, B=100. The purified fragments were sequenced on a gas phase protein sequencer (Applied Biosystems model 470A) with an on-line PTH analyzer (Applied Biosystems, model 120A). The sequence is provided in Seq. I.D. No. 2.

C. Assay of ADP-ribosylarginine hydrolase

Purified rat brain hydrolase (0.04 µg) was assayed in 50 mM potassium phosphate, pH 7.5/5 mM dithiothreitol/10 mM $MgCl_2$/0.1 mg ovalbumin/50 µM ADP-ribosyl-[$^{14}$C] arginine (6000 cpm)(total volume, 100 µl). After 30 min at 30° C, a sample (80 µl) was applied to a column (0.5×4 cm) of Affi-Gel 601 (boronate) equilibrated and eluted with 0.1M glycine, pH 9.0/0.1M NaCl/10 mM $MgCl_2$ (5 ml). The total eluate was used for liquid scintillation counting. One unit corresponds to one µmol of ADP-ribosylarginine hydrolyzed per min.

ADP-ribosyl-[$^{14}$C]arginine was generated in a mixture containing turkey erythrocyte ADP-ribosyltransferase (120 µg; 17.83 µmol.min$^{-1}$mg$^{-1}$), 50 mM Tris-HCl, pH 7.5/10 mM NAD/100 mM NaCl/2 mg ovalbumin/20 mM [$^{14}$C] arginine (25 µCi) (total vol., 2 ml). Reaction was initiated with turkey erythrocyte ADP-ribosyltransferase, incubated for 40 min at 30° C, and then applied to a column (1×3 cm) of Affi-Gel 601 which was washed with 0.1M glycine, pH 9.0/0.1M NaCl/10 mM $MgCl_2$ (30 ml) and eluted with 0.05M sodium acetate, pH 5.0 (2 ml fractions) into tubes containing 0.2 ml of 1M Tris-HCl, pH 7.5. The turkey erythrocyte ADP-ribosyltransferase was purified as described in Moss, et al., *J. Biol. Chem.* 254:8891–8894 (1979).

EXAMPLE 2

Expression of Rat Brain ADP-ribosylarginine Hydrolase cDNA

A. Isolation of rat brain ADP-ribosylarginine hydrolase cDNA

To isolate rat brain ADP-ribosylarginine hydrolase cDNA a Lambda ZAP II rat brain cDNA library (from Stratagene) with titer of 1.4×10$^{10}$ pfu/ml, was screened in *E. coli* XL-1 Blue cells, by plaque hybridization (~6×10$^5$ plaques) with the 21-mer oligonucleotide probe of Seq. I.D. No. 3.

For the initial screening, nylon filters from duplicate lifts of 2 min and 4 min were used. The filters were denatured in 1M NaOH, 1.5M NaCl, neutralized in 1M Tris, 1.5M NaCl, baked at 80° C. for 2 h under vacuum and prehybridized for 4 hr at 42° C. in 5x SSC (1X=0.15M NaCl/0.015M sodium citrate)/5X Denhardt's solution (1X=0.02% Ficoll/0.02% polyvinylpyrrolidone/0.02% bovine serum albumin)/10 mM Tris-HCl pH 7.4/10% dextran sulfate/0.5% SDS/denatured salmon sperm DNA (100 µg/ml). Hybridization was carried out for 18 h at 42° C., using fresh prehybridization solution, with probe, which was labeled at the 3' end with $^{32}$P using terminal deoxynucleotidyltransferase, at a concentration of 1×10$^6$ cpm per filter. After hybridization, filters were washed twice with 2X SSC/0.5% SDS at room temperature and twice with 0.5×SSC/0.5% SDS at 42° C. for 20 min. Filters were exposed to Kodak XAR-2 film overnight at −80° C. with intensifier screens.

Clones which hybridized very strongly with both probes of Seq. I.D. Nos. 3 and 4 were isolated and excised in vivo according to the protocol of Short et al., *Nucl. Acids Res.* 16:7583–7600 (1988). Colonies appearing on the plates contain the Bluescript plasmid with the cloned DNA insert. Several colonies from the plates were selected and grown in 40 ml of LB/Amp at 37° C. The DNA from the cultures was purified according to the QIAGEN (Chatsworth, Calif.) protocol.

In our work, the probed sequence was not an intact gene and the following procedures were employed to obtain an intact gene.

The resulting cDNA pellets were digested with EcoR1 and yielded inserts consistent with internal EcoR1 sites. One clone yielded two inserts of ~520-bp and ~450-bp, and another clone yielded one insert of ~1100-bp and two smaller inserts of ~200-bp, consistent with internal EcoR1 sites. Each clone was sequenced in both directions, using Sequenase reagents from United States Biochemicals and protocols as previously described in Price, et. al, *Proc. Natl. Acad. Sci. U.S.A.*, 85:5488–5491 (1988). Analysis with Microgenie (from Beckman) revealed that the two independent clones had an overlap of ~450-bp. The first clone overlapped the nucleotide sequence of probe No. 3 used for screening and also contained the ATG initiation codon, whereas the second clone started only 62-bp downstream from the ATG initiation codon of the first clone and contained the TAG stop codon.

To generate a cDNA encompassing the complete hydrolase coding region, cDNA from the two clones was amplified and joined by overlap extensions through a series of 3 PCRs (similar to the strategy described by Higuchi, *PCR Technology: Principles and Applications for DNA Amplification*, 61–70 (Erlich, ed. 1989).

In PCR #1, primers of Seq. I.D. No. 5 and Seq. I.D. No. 7 were used to amplify a 351-bp segment of the first clone which included the ATG start codon. In PCR #2, primers of Seq. I.D. No. 6 and Seq. I.D. No. 8 were used to amplify a 816-bp segment of the second clone. These segments resulting from PCR #1 and PCR #2 had a 78-bp overlap. After spin dialysis on Centricon-100 (Amicon, Beverly, Mass.), the cDNA segments were mixed in a 1:1 ratio and reamplified in PCR #3 using the end primers of Seq. I.D. No. 5 and Seq. I.D. No. 6 resulting in a cDNA encompassing the entire ~1086-bp coding region, together with the TAG stop codon and additional sequences for BamH1 and EcoR1. Each PCR (Perkin-Elmer Thermal Cycler) was run for 25 cycles (1 min, 94° C.; 1 min, 56° C.; 1 min, 72° C.).

B. Expression of ADP-ribosylarginine hydrolase cDNA in *E. coli*

The ADP-ribosylarginine hydrolase cDNA was digested with BamH1 and EcoR1. The resulting ~1086 bp insert was ligated into the BamH1- and EcoR1-digested pGEX-2T vector (from Pharmacia) at room temperature for 4 h and then at 16° C. overnight in ratios of vector to insert of 1:1, 1:3 and 1:5 using 100 ng of pGEX-2T (in 10 µl).

The ligated products were diluted 1:5 with 10 mM Tris, pH 7.4/0.1 mM EDTA and 5 µl were mixed with 100-µl samples of competent cells (*E. coli* DH5α). The cells were incubated on ice for 30 min, and then heat-shocked at 37° C. for 40 s without shaking. Samples were returned to ice for 2–3 min. Following addition of LB (0.9 ml), cells were incubated at 37° C. for 1 h with vigorous shaking. Samples (150 µl) of each culture were applied to LB/AMP plates, which were incubated at 37° C. overnight. Some of the resulting colonies were analyzed by PCR, and lifts prepared from the remaining plates were hybridized with hydrolase oligonucleotide of Seq. I.D. No. 8.

Transformants were screened by two techniques. The first involved a PCR-based analysis. Colonies, picked from plates, were grown overnight in 5 ml of LB/AMP at 37° C. Cultures (30 µl) were transferred to 0.5-ml conical PCR tubes. After centrifugation (Microfuge, 2 min, 10,000 rpm), the supernatant was discarded, 20 µl of PCR mix (see below) was added to the pellet followed by 20 µl of mineral oil and PCR was carried out for 30 cycles (94° C., 1 min; 56° C., 2 min; 72° C., 1 min) followed by extension at 72° C. for 7 min. The PCR mix contained 80 µl of 10X buffer, 80 µl of dNTP mix (each 2 mM), 8 µl of 10% Tween, 8 µl of Seq. I.D. No. 5 primer (800 ng), 8 µl of Seq. I.D. No. 6 primer (800 ng), 8 µl of Taq polymerase (400 units, from Promega), and 608 µl of $H_2O$. PCR reaction products (10 µl) were analyzed on a 1% agarose gel.

The second method for analysis of transformants involved colony hybridization. Nytran filters were prewetted on LB/AMP plates for 30 s and transferred to plates containing the colonies for 30 s, then transferred again to the LB/AMP plates that were used for prewetting. Colonies were allowed to grow overnight at room temp. The next morning the Nytran filters were washed with 10% SDS, placed in a denaturation solution containing 1N NaOH/1.5M NaCl, neutralized in 1M Tris, pH 8/1.5M NaCl, rinsed in 2X SSC, dried for 2 h at 80° C. under vacuum, washed for 20 min with 5X SSC to remove agar, prehybridized and hybridized as described.

For hybridization, an 18-mer oligonucleotide (Seq. I.D. No. 8) was labeled at the 3' end using terminal deoxynucleotidyltransferase. Three colonies positive by hybridization and four positive by PCR were grown overnight at 37° C. Cultures were diluted 1:10 in 2 ml of LB/AMP, grown at 37° C. for 1 h, and induced with 0.1 mM IPTG for 2 h at 37° C. (36). Following centrifugation for 2 min at 10,000 rpm, supernatants were discarded and pellets were mixed with 50 µl of 2X SDS sample buffer (4% SDS/2x 10% glycerol/ 0.02% bromophenol blue/1% β-mercaptoethanol/125 mM Tris, pH 6.8) and boiled for 10 min. Samples were subjected to electrophoresis in a 4–20% gradient Tris-glycine gel for 2 h at 125 volts, with high molecular weight standards. Two transformants produced a putative fusion protein of ~65 kDa.

EXAMPLE 3

Purification of ADP-ribosylarginine Hydrolase

A. Affinity purification of fusion protein

Overnight cultures, grown at 37° C. from single colonies, were diluted 1:10 in LB/Amp, grown for 1 h at 37° C., and induced with 0.1 mM IPTG for 1 or 2 h. Cultures (2 ml) were centrifuged (Microfuge, 14,000 rpm, 10 s). Supernatants were discarded and pellets were suspended in 300 µl of ice-cold PBS and the suspensions were sonicated three times for 15 s on ice. 10% Triton X-100 (30 µl) was added and the samples were mixed (vortex) twice for 30 s, before centrifugation (Microfuge, 5 min). Pellets were suspended in 300 µl of PBS and samples (30 µl) were mixed with 30 µl of 2X SDS sample buffer and analyzed by SDS-PAGE. To the remainder, 50 µl of a 50% slurry of glutathione-agarose beads were added followed by mixing at room temperature for 45 min on a rotary mixer.

PBS was added to a total volume of 1 ml followed by mixing (vortex) for 30 s, and centrifugation for 10 s. The beads were washed twice with PBS, and the fusion protein was eluted by boiling the beads for 10 min with 25 µl of 2X SDS/sample buffer.

B. Thrombin digestion of the hydrolase fusion protein

Cultures (5 ml) from single colonies of one transformant were grown overnight at 37° C., diluted 1:100 into 100 ml of LB/AMP and grown for 2–2.5 h until $OD_{600}$=0.4–0.5. After addition of 0.1 mM IPTG, cultures were incubated for 2 h at 37° C., and centrifuged (5 min, 1200 xg). The pellet was suspended in 3 ml of cold PBS and sonicated three times for 30 s on ice. 10% Triton X-100 was added (2% final concentration), followed by mixing (vortex) for ~2 min and centrifugation (1200 xg, 5 min). The supernatant was applied to a prepacked glutathione-Sepharose 4B column (1.5×1.2 cm).

The column was washed twice with 7.5 ml PBS, and then the fusion protein was eluted with 10 ml of 50 mM Tris-HCl, pH 8.5 mM glutathione. Fractions containing the fusion protein (determined by electrophoresis) were combined; fusion protein was estimated to be ~0.5 µg/20 µl. The total volume (2.5 ml) was concentrated to ~100 µl in a Centricon-10 which had been soaked in 1 ml of a solution of bovine serum albumin (200 µg), then washed with water and twice with 1M NaCl/20 mM Tris, pH 8/5 mM EDTA.

The buffer was exchanged with the thrombin cleavage buffer (150 mM NaCl/2.5 mM $CaCl_2$/50 mM Tris, pH 8) by adding 1 ml of cleavage buffer and Concentrating to ~100 µl. A 10-µl sample was saved for electrophoresis and to the remaining 90-µl, human thrombin was added at a ratio (w:w) of 1:50 to fusion protein and the mixture was incubated at 25° C. for 1-1/2 h. A sample (10 µl) was saved for electrophoresis and to the remainder, 50 µl of a 50% slurry of glutathione-agarose beads were added. After incubation at room temperature for 45 min and centrifugation, an equal volume of 2X SDS/sample buffer was added to the beads. Gel electrophoresis indicated the presence of the desired ADP-ribosylarginine hydrolase.

EXAMPLE 4

Isolation of Mouse ADP-ribosylarginine Hydrolase

The nucleic acid sequence encoding mouse brain ADP-ribosylarginine hydrolase was determined by a series of PCRs.

To determine nucleotides 291–760 (based on the rat gene sequence with A of ATG equal to 1), primers corresponding to bases 273–290 sense and bases 761–788 antisense (in the rat brain sequence, with A of ATG equal to 1) were amplified on mouse brain cDNA template for 25 cycles (95° C., 1 min/50° C., 1 min/72° C., 1 min) followed by 7 min of extension at 72° C. The resulting product was re-amplified using the primers above (94° C., 1 min/72° C., 2 min; 35 cycles then extension at 72° C. for 7 min) to provide a more uniform amplified product.

Similarly, to determine bases 688–1094, PCR was carried out with primers corresponding to bases 671–687 (mouse sequence) and 1095–1112 (rat sequence, with A of ATG equal to 1) on mouse brain cDNA template (95° C., 1 min/50° C., 1 min/72° C., 1 min; 25 cycles then 7 min extension at 72° C.). Again, reamplification using this product (94° C., 1 min/52° C., 1 min/72° C., 2 min; 30 cycles, then 7 min extension at 72° C.) provides a more uniform product.

Bases 1–370 were determined using a similar protocol. PCR amplification was carried out using primers corresponding to bases −26—10 (rat sequence, sense, with A of ATG equal to 1) and 423–439 (mouse sequence, antisense) with mouse brain cDNA template (95° C., 1 min/55° C., 1 min/72° C., 1 min; 25 cycles, then 7 min extension at 72° C.). The resulting product was re-amplified using primers corresponding to bases −26—10 (rat sequence, sense, with A of ATG equal to 1) and 371–387 (mouse sequence, antisense) and identical conditions.

The mouse brain nucleic acid sequence encoding ADP-ribosylarginine hydrolase is listed in Seq. I.D. No. 9.

EXAMPLE 5

Isolation of Human ADP-ribosylarginine Hydrolase

A PCR fragment corresponding to bases 418–912 (relative to the rat brain sequence of Seq. I.D. No. 1, with A of ATG equal to 1) was synthesized in a series of PCRs to generate a probe for screening a human cDNA library.

The human sequence corresponding to bases 201–912 was amplified using primers of bases 187–200 (rat sequence, sense, with A of ATG equal to 1) and 913–933 (rat sequence, antisense, with A of ATG equal to 1) with human brain cDNA (from Clontech). Twenty five cycles were run (94° C., 1 min/50° C., 1 min/72° C., 2 min) followed by extension at 72° C. for 7 min.

The resulting PCR reaction mixture was re-amplified under identical conditions using primers of bases 397–416 (rat and mouse sequence, with A of ATG equal to 1) and 913–933 (rat sequence, with A of ATG equal to 1).

The amplified product was gel-purified and used as template in a PCR with the immediately preceding primers for 20 cycles (94° C., 1 min/60° C., 1 min/72° C., 1 min) followed by extension for 72° C. for 7 min. The resulting product was gel-purified and resubjected to PCR under conditions just described.

Purification, subcloning and sequencing under standard conditions provides the probe corresponding to bases 418–912 of the partial human cDNA of Seq I.D. No. 11.

To isolate human cDNA encoding ADP-ribosylarginine hydrolase, a Lambda ZAP II human fetal brain cDNA library (from Stratagene) was screened. Using the above probe and the method of Example 2 with only minor modification (stringency: 10 mM Tris, pH 7.5/5×SSC/0.1% SDS, 50% formamide/5x Denhardt's/10% dextran sulfate and wash: 2×SSC/0.5% SDS, room temperature for 10 min with 0.5× SSC/0.5% SDS, 42° C., 15 min×2) a cDNA encompassing over 90% of the human hydrolase coding region was isolated and has a sequence as set forth in Seq. I.D. No. 11. The missing portion of the cDNA (~17 amino acids) is obtained using conventional means as described herein.

---

What is claimed is:

1. An isolated nucleic acid which consists of a sequence selected from the group consisting of Seq. I.D. No. 1, Seq. I.D. No. 9 and Seq. I.D. No. 11.

2. An isolated nucleic acid consisting of a sequence selected from the group consisting of SEQ ID NO:1, SEQ ID NO:9 and SEQ ID NO:11, operably linked to a promoter.

3. A nucleic acid of claim 1, wherein the nucleic acid is contained in an expression cassette.

4. A method of producing a mammalian ADP-ribosylarginine hydrolase by introducing into a suitable host cell an expression cassette having a promoter sequence operably linked to a DNA sequence consisting of sequences selected from the group consisting of Seq. I.D. No. 1 and Seq. I.D. No. 9 or to a human sequence encoding only a hydrolase wherein approximately 90% of the sequence is Seq. I.D. No. 11, and expressing said DNA sequence to produce said mammalian ADP-ribosylarginine hydrolase.

5. A method of claim 4 wherein said suitable host cell is a bacterial cell.

6. A method of claim 4 wherein said suitable host cell a *E. coli* cell.

7. A method of claim 4 wherein said suitable host is a mammalian cell.

8. A method of isolating from mammalian tissue a DNA sequence encoding ADP-ribosylarginine hydrolase comprising, probing a DNA library prepared from mammalian tissue with an oligonucleotide probe which binds to a conserved portion of the nucleic acid of the rat brain ADP-ribosylarginine hydrolase cDNA within bases 418 to 912 of Seq. I.D. No. 1, wherein said probe is able to detect cDNA encoding ADP-ribosylarginine hydrolase with less than 1% false positives during the probing of the library, and separating any DNA sequence which binds to said probe.

9. A method of claim 8 wherein the mammalian tissue is selected from the group of mammals consisting of:

(a) humans;

(b) rats; and (c) mice.

10. A method of claim 8 wherein the mammalian tissue is human tissue.

11. A method of claim 8 wherein the mammalian tissue is rat tissue.

12. A method of claim 8 wherein the mammalian tissue is mouse tissue.

13. A method of claim 8 wherein the DNA library comprises cDNA.

14. A method of claim 8 wherein the DNA library comprises genomic DNA.

* * * * *